(12) United States Patent
Wysokowski et al.

(10) Patent No.: US 7,423,754 B2
(45) Date of Patent: Sep. 9, 2008

(54) WEB PLANARITY GAUGE AND METHOD

(75) Inventors: John P. Wysokowski, Fairport, NY (US); Scott E. Stickel, Rochester, NY (US); Alan R. Bentz, Bergen, NY (US)

(73) Assignee: Eastman Kodak Company, Rochester, NY (US)

( * ) Notice: Subject to any disclaimer, the term of this patent is extended or adjusted under 35 U.S.C. 154(b) by 28 days.

(21) Appl. No.: 11/622,015

(22) Filed: Jan. 11, 2007

(65) Prior Publication Data

US 2008/0170237 A1 Jul. 17, 2008

(51) Int. Cl.
*G01N 21/84* (2006.01)
(52) U.S. Cl. ...................................... 356/429
(58) Field of Classification Search ........................ None
See application file for complete search history.

(56) References Cited

U.S. PATENT DOCUMENTS 5,073,712 A * 12/1991 Hellstrom ................. 250/252.1
5,457,539 A * 10/1995 Sturm ......................... 356/429
5,778,724 A 7/1998 Clapp et al.
6,757,064 B2 * 6/2004 Eisen et al. ................. 356/429
2004/0021869 A1 * 2/2004 Shakespeare et al. ........ 356/429

OTHER PUBLICATIONS

2002 PFFC Peer-Reviewed Paper, "Baggy Webs: Making, Measurement and Mitigation Thereof", by David R. Rosium, Ph.D., Finishing Technologies, Inc., published Apr. 2002.

* cited by examiner

*Primary Examiner*—Michael P Stafira
(74) *Attorney, Agent, or Firm*—Stephen H. Shaw

(57) ABSTRACT

An apparatus for measuring web planarity includes a horizontal reference surface and a light source for projecting a light pattern onto the reference surface at an angle. A web is supported above the reference surface. An imaging device detects (1) positions on the reference plane of interception of discrete regions of the projected light pattern and (2) respective positions on the web of interception of the same discrete regions of the projected light pattern. The imaging device determines the vertical offset of the respective positions on the web as a function of differences in the detected positions on the reference plane and the respective detected positions on the web. A measure of non-planarity of the web is calculated based upon a comparison of a plurality of such vertical offsets from a plurality of detected positions of the web.

11 Claims, 21 Drawing Sheets

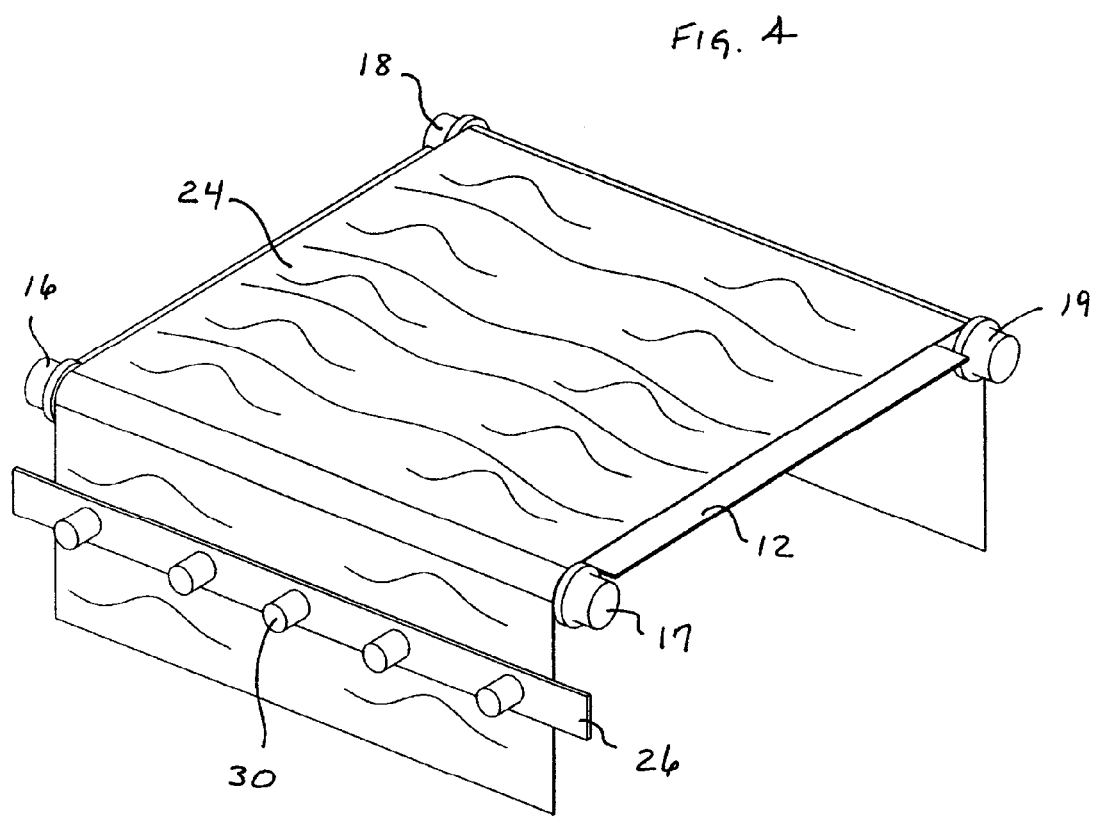

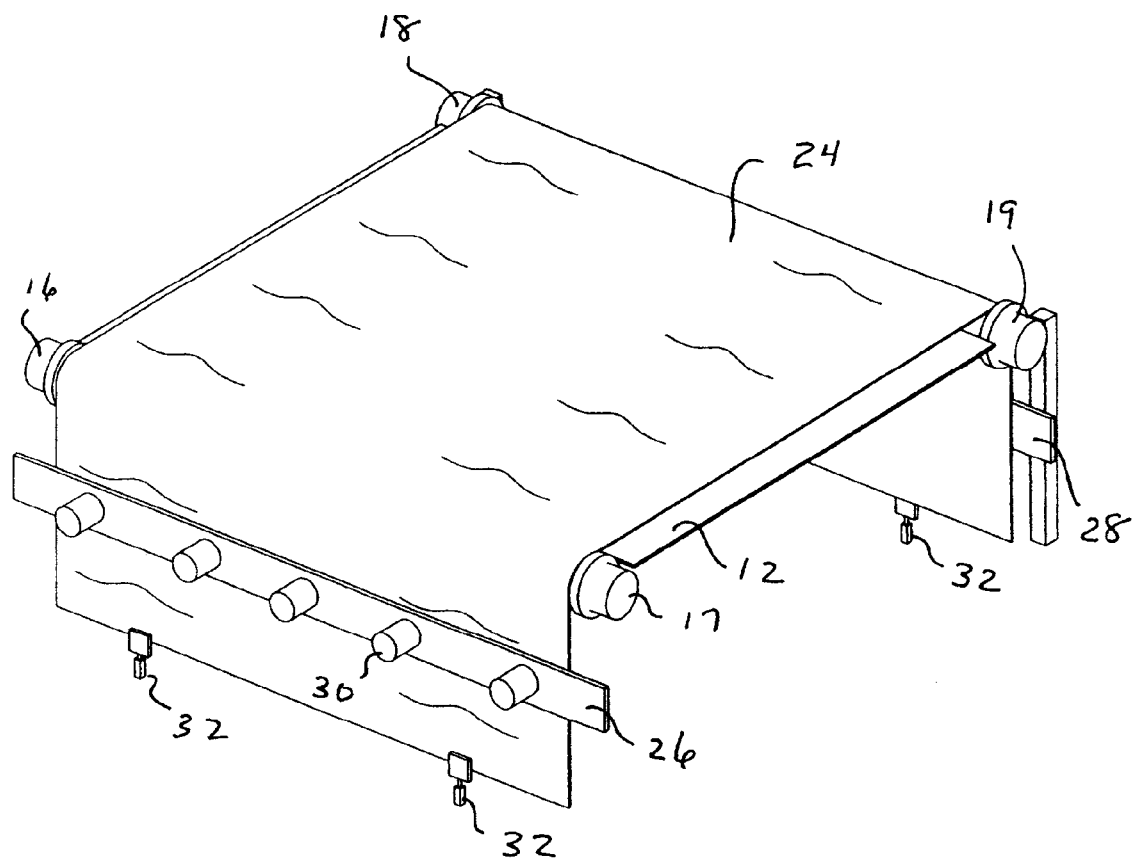

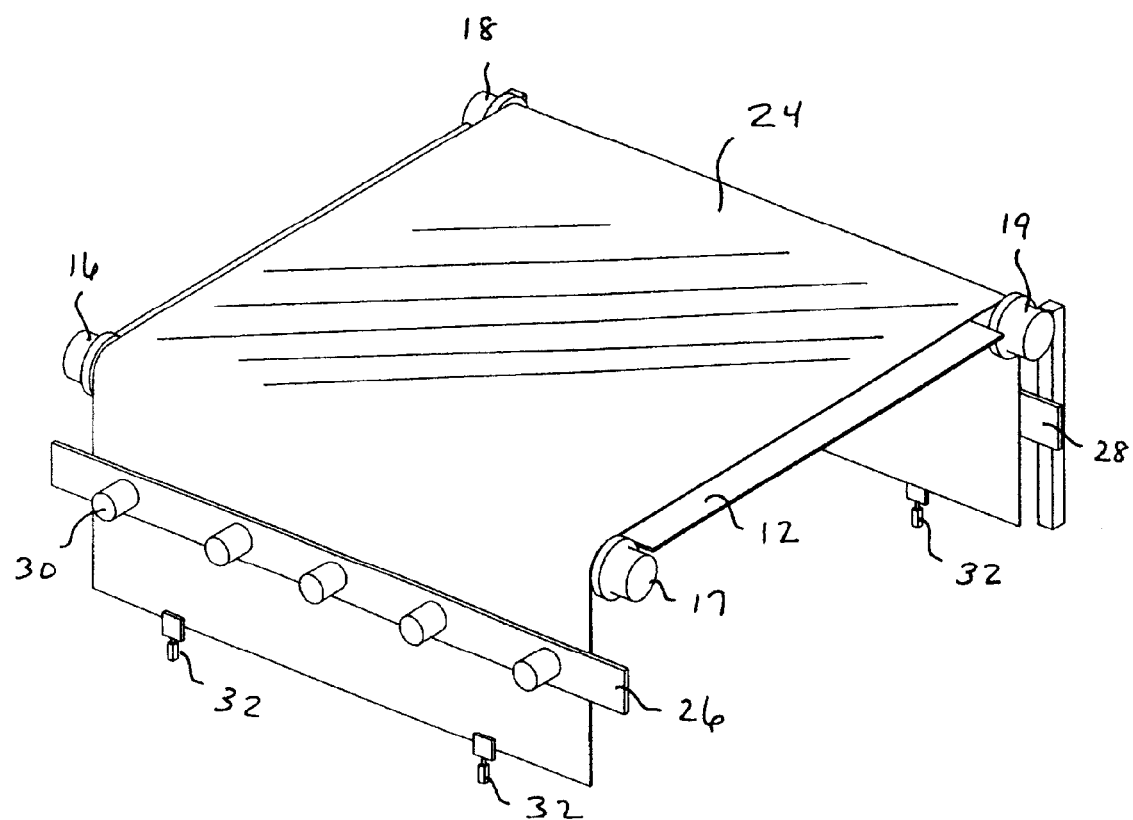

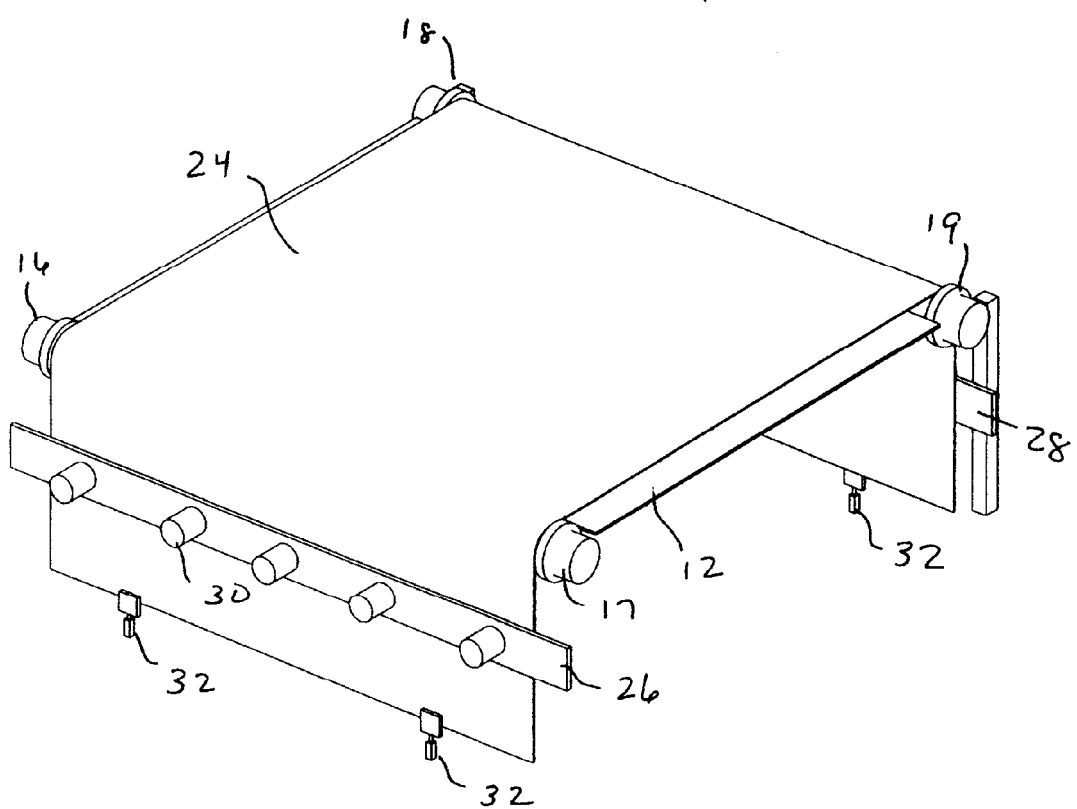

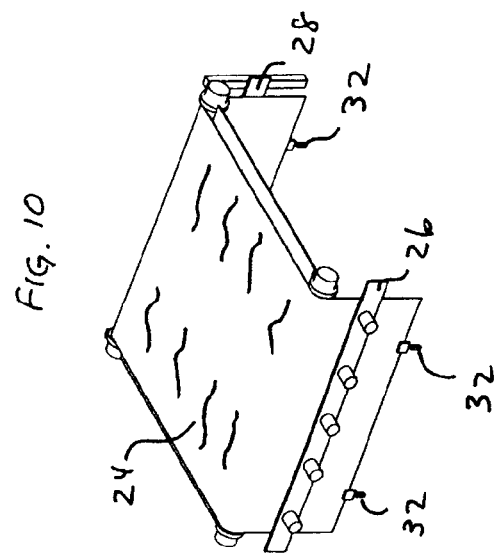
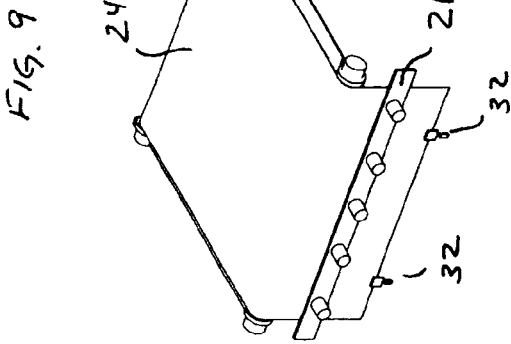
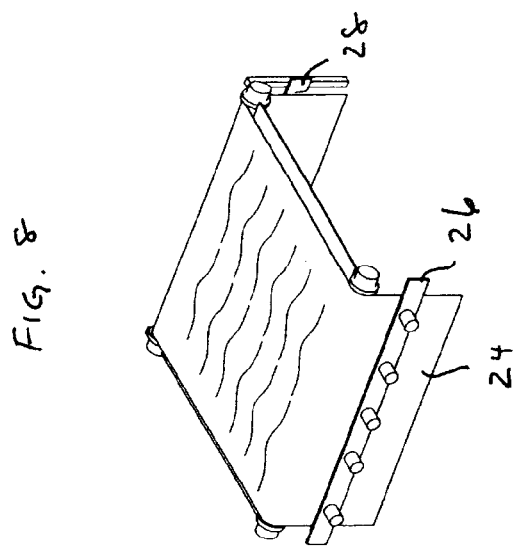

WEB PLANARITY GAUGE AND METHOD

FIELD OF THE INVENTION

The present invention relates to measuring or quantifying the bagginess of webs.

BACKGROUND OF THE INVENTION

Paper materials, plastic film materials, and other materials commonly provided in sheet and strip form are often initially produced as continuous lengths of material, usually referred to as "webs," which are wound onto cores. As used herein, the term "web" is intended to refer both to such continuous lengths of material and to shorter and narrower, so called "sheets" of material. During manufacture, the web can stretch or shrink unevenly across the cross-web (CD) direction and in the machine direction (MD) of the web. When the web returns to its steady-state condition, the stretched or shrunken areas will often become baggy, which can develop into creases or wrinkles in the web. These changes in the condition of the web can cause problems in later web handling operations, including conveying through nips, slitting and winding. For example, it is more difficult to properly slit a baggy web into strips than to slit a web without bagginess.

According to David R. Roisum, in his 2002 PFFC Peer-Reviewed Paper entitled "BAGGY WEBS: MAKING, MEASUREMENT AND MITIGATION THEREOF," bagginess can be defined as a deviation of flatness. That is, web that refuses to lay or run flat and straight is said to be baggy. Depending on the particular industry, bagginess is also related to terms such as "baggy lanes", "camber", "frogbellies", "layflat", "puckers", and "non-planarity".

Bagginess in a web poses several difficulties including poor visual appearance, defects during coating or lamination, impediments to floating over rollers, differences in winding tightness, and problems in web guiding, tracking and path control. A web having excessive bagginess may refuse to go through nips.

Bagginess is very difficult to measure in a quantifiable way. Common instruments and measurements do not correlate well to bagginess because they do not measure anything closely related to it. While there are ways to measure bagginess more directly, most are tedious or fraught with uncertainty or both. Thus, culling and rejection is typically done by subjective visual inspection.

One test for bagginess involves laying a web on an inspection table whereby the web is under no external stresses that can disturb flatness. A baggy web will not lay flat and/or the edges will not be straight. Roisum suggests that the most important or effective tool for bagginess detection is the eye of the operator. Baggy edges will appear as ruffles. A baggy lane will appear as stitches or "tractor tire" marks oriented in the machine direction. However, Roisum recognizes that a web can appear to be baggy when it is not because hard wrinkles and curl can cause the web to not lay dead flat even if it is not inherently baggy. Thus, a more rigorous test for inherent bagginess is needed.

Another method of monitoring bagginess of a web is disclosed in U.S. Pat. No. 5,778,724, which issued to T. Clapp et al. on Jul. 14, 1998. In the Clapp et al. method, a first reference light is projected onto a front face of the web transverse to the web, and a first measurement light is projected onto the front face of the web non-perpendicular to the front face and transverse to the web. The longitudinal distance on the front face of the web between a point along the first reference light and a corresponding point along the first measurement light are compared to determine bagginess of the web. In the Clapp et al. process, two laser line sources are required: one that is normal to the web in the cross-direction and another that grazes the web in the cross-direction. Relative distance between the lines indicates extent of bagginess. This is primarily an "on-line" tool. Only a single line of cross-direction web bagginess information is collected at a time. The method does not attempt to reconstruct the three-dimensional surface, as very simple two-dimensional geometry math is used. Clapp et al. make no reference to a need to control web tension. For such an on-line system, the minimum amount of tension that is needed to convey the web may indeed be too high to expose problematic bagginess (i.e., non-planarity). Even minor amounts of non-planarity can cause severe problems in subsequent finishing operations requiring conveyance of adjacent web slits through nip rollers and crosscut sheeters.

Accordingly, there exists a need to control web tension at a level much lower than the typical paper manufacturing process in order to expose and measure small degrees of non-planarity that are not visible at higher tensions. There is also a need to use multiple lines, in order to gather significantly more information about true non-planarity, and analyze and reconstruct the entire surface topology of a 2D section of web.

SUMMARY OF THE INVENTION

According to a feature of the present invention, an apparatus for measuring web planarity includes a reflective reference surface lying in a horizontal plane and a light source adapted to project a light pattern onto the reference surface along a non-vertical axis. The light pattern has discrete regions that intercept the reference surface. A support is adapted to receive a web and to bear the received web vertically offset from the reference surface such that the received web intercepts the discrete regions of the projected light pattern. An imaging device is adapted to detect (1) positions on the reference plane of interception of the discrete regions of the projected light pattern and (2) respective positions on the received web of interception of the same discrete regions of the projected light pattern. The imaging device determines the vertical offset of the respective positions on the received web as a function of differences in the detected lateral positions on the reference plane and the respective detected lateral positions on the received web. A measure of non-planarity of the received web is calculated based upon a comparison of a plurality of such vertical offsets from a plurality of detected positions of the received web.

In a preferred embodiment, the support is a pair of parallel rollers on opposed sides of the reference surface. The rollers may have guide flanges at one end. The support may further comprise a tensioner for applying a predetermined tension to the web.

According to another feature of the present invention, a method of measuring web planarity includes the steps of providing a reflective reference surface and adjusting the reference surface to be level in a horizontal plane; projecting a light pattern of discrete regions onto the reference surface along a non-vertical axis so as to intercept the reference surface; supporting a web spaced vertically above the reference surface such that the received web intercepts the discrete regions of the projected light pattern; detecting positions on the reference plane of interception of the discrete regions of the projected light pattern; detecting respective positions on the received web of interception of the same discrete regions of the projected light pattern; determining the vertical offset of the respective positions on the received web as a function of differences in the detected lateral positions on the reference plane and the respective detected lateral positions on the received web; and calculating a measure of non-planarity of the received web based upon a comparison of a plurality of such vertical offsets from a plurality of detected positions of the received web.

BRIEF DESCRIPTION OF THE DRAWINGS

FIG. 4 is a perspective view of a baggy sample with core set before weights are attached to its corners;

FIG. 5 is a perspective view, similar to FIG. 4, after weights are attached to its corners;

FIG. 6 is a perspective view of a misaligned sample;

FIG. 7 is a perspective view, similar to FIG. 6, but of a properly aligned sample;

FIG. 8 is a perspective view showing a baggy web before tension is applied;

FIG. 9 is a perspective view similar to FIG. 8 showing the effect of too much applied tension;

FIG. 10 is a perspective view similar to FIGS. 8 and 9 showing the correct amount of applied tension;

DETAILED DESCRIPTION OF THE INVENTION

Referring to FIGS. 1, 2, 3, 3A and 3B, a near roller 10 is aligned with a second, far roller 14. The top surface of table 12 is preferably painted white for maximum reflectivity and lies in a horizontal plane. Terms of horizontal orientation such as "near", "far", "left", "right", etc. are used as an aid to understanding the apparatus being described herein, and are not intended to imply any particular orientation of the apparatus during manufacture or use. However, terms of vertical orientation such as "top", "bottom", "above", "below", up "down", etc. do have significance in the description and the appended claims. Also, the phrases "machine direction" (MD) and "cross-web direction" (CD) are intended to respectively connote the direction of web movement from a supply roll and the direction normal to that of web movement from a supply roll, respectively. Both MD and CD directions lie in the plane of the web.

Measurements taken by the apparatus according to the present invention are intended to be extremely accurate and reliable to quantify flatness of a web material. Flatness is measured and displayed in basic engineering units of differential length per unit length (dL/L) in the machine direction as a function of cross-web direction location. Typical units are microns per meter, but other units may be used. To attain precision results, it is important that care be taken to assure that table 12 be as flat as possible. If the table sags in the middle, for example, and the web were perfectly flat, a three-dimensional plot of web height above the table would appear as the inverse of the tabletop sag. This is because the analysis program assumes that the table is perfectly flat. During experimental measurements of a 54" wide web, the inventors first used a simple 0.12" thick aluminum sheet as the table and noted this problem. They then converted to a 0.50" thick aluminum jig plate that was ground flat on both sides to resolve this issue.

Figure 1:
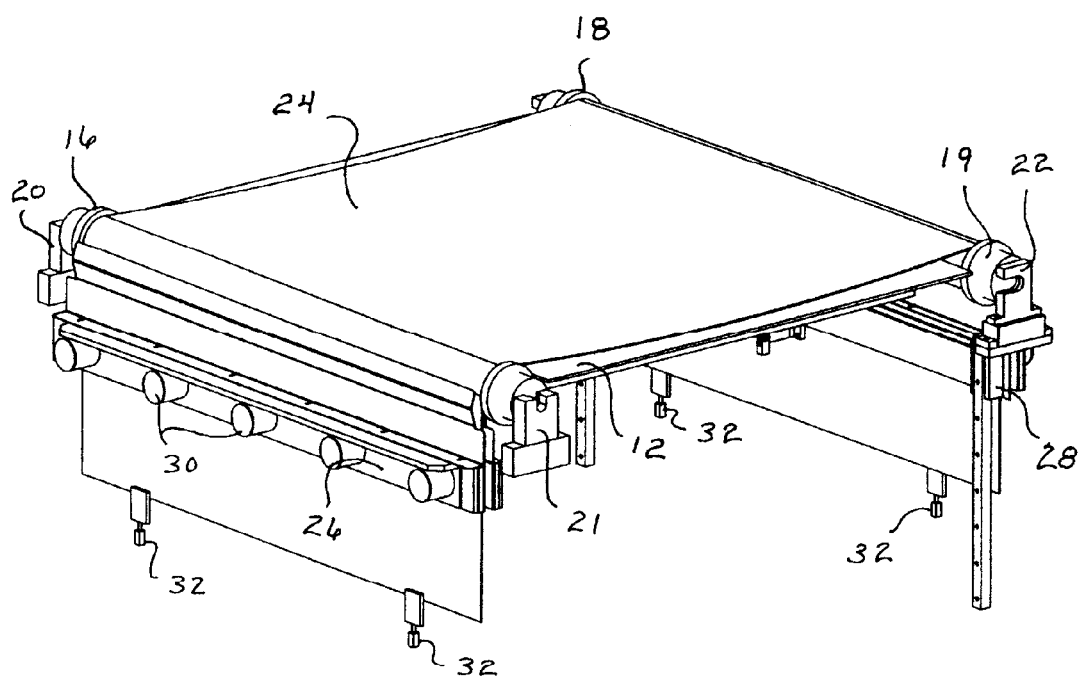
FIG. 1 is a perspective view of a portion of a planarity gauge according to the present invention.
Figure 2:
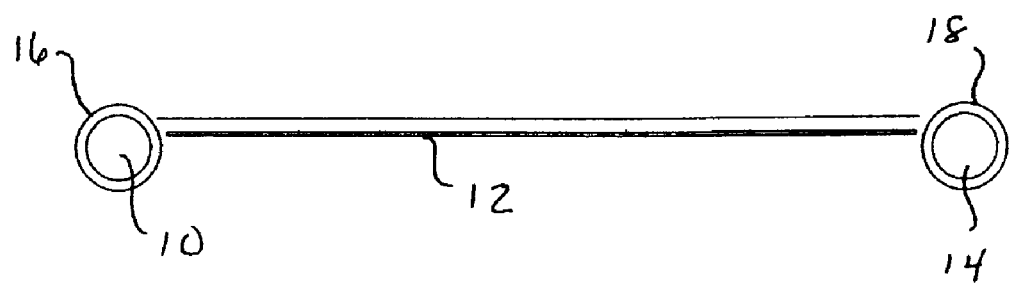
FIG. 2 is a side elevation view of a portion of the planarity gauge of FIG. 1.

Rollers 10 and 14 have guide flanges 16-19 at their ends. Near roller 10 rotatably sits in bearing blocks 20 and 21, while far roller 14 is carried in opposed load cells 22, of which one is shown in FIG. 1. The horizontal distance between the rollers must be precisely set to be uniform. During development, uniformity to within 0.002" appeared to give satisfactory results for a 54" wide web. The rollers and tabletop are also aligned in the vertical plane using a precision level.

After machine calibration, to be discussed later in this writing, and in preparation for a planarity measurement, a web sample 24 is draped over rollers 10 and 14 inside of flanges 16-19. The near end of web 24 is placed between opposed halves of an open stationary clamp 26, while the far end of web 24 is placed between opposed halves of an open movable clamp 28. The ends of the web must extend beyond the clamps and be accessible. Clamps are not closed yet.

Small preload weights 32 are clipped to the ends of web 24, two per end, near each edge of the web. This preloading is desirable to assure an accurate measurement by preventing web sample web 24 from shifting as the clamps close. The operator now makes sure that all four preload weights and both web ends are hanging freely and not touching anything, including the frame, floor, pneumatic tubing, etc. Preloading also removes some of the waviness (e.g. core set) in the web (shown in FIG. 4) that is not due to bagginess. FIG. 5 illustrates the web after the preload weights are attached and while the clamps are open.

Figure 3A:
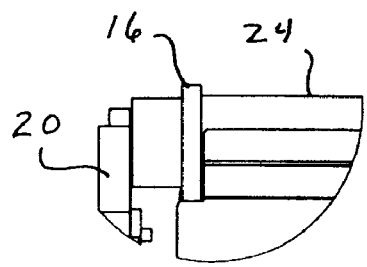
FIG. 3A is a detail view of a portion of the planarity gauge within circle A of FIG. 3.
Figure 3B:
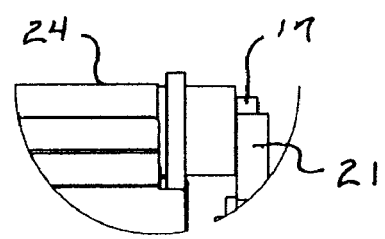
FIG. 3B is a detail view of a portion of the planarity gauge within circle B of FIG. 3.
Figure 3:
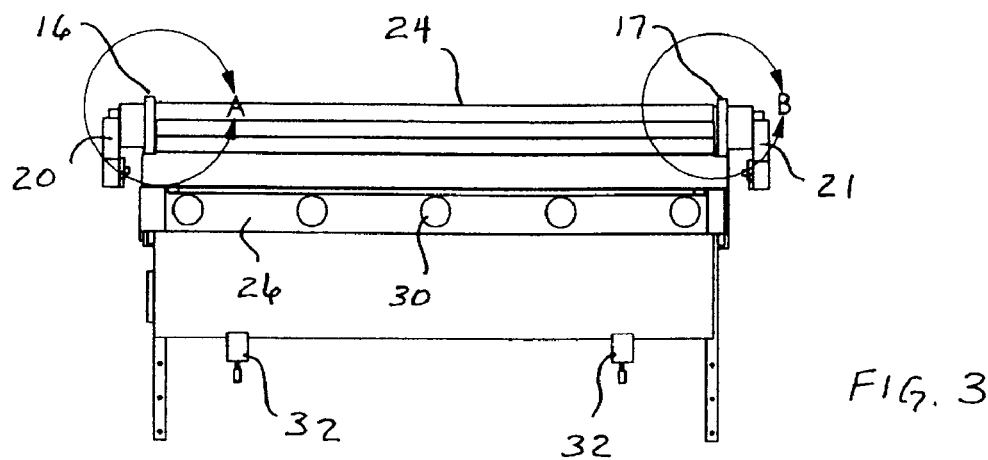
FIG. 3 is a front elevation view of a portion of the planarity gauge of FIG. 1.

Web sample web 24 is gently slid up against guide flanges 16 and 18 as shown in FIG. 3A. The web should touch only at very top of each roller (the so called 12 o'clock position), being sure that web is right up against both flanges without being crumpled. FIG. 3B shows that the web has been pulled away from guide flanges 17 and 19 by this step. Failure to align sample properly will result in a misaligned sample as illustrated in FIG. 6 and will result in large diagonal draw lines when tension is applied and will require unclamping and returning to this step. A properly aligned sample is shown in FIG. 7.

Stationary clamp 26 is now closed by suitable means readily selectable by one of ordinary skill in the art. For example, the illustrated embodiment uses a series of clamping air cylinders 30 for this purpose. A web tensioner draws web 24 by moving clamp 28 downward after clamps 26 and 28 are closed. The amount of tension in the web is predetermined to be sufficient to remove any core set in the web material that would introduce noise into the results of the subsequent planarity measurement. The predetermined tension should be less than the planned operating tension for the web from which the sample was cut, and should be low enough to still be able to see all non-planarity defects in the web. FIGS. 8, 9 and 10 illustrate this procedure. FIG. 8 shows web 24 unclamped. Note the existence of bagginess. FIG. 9 shows the web when too much tension is applied. All core set and bagginess wrinkles have been removed, and will result in a false result. In FIG. 10, the proper amount of tension has been applied to remove the core set while retaining most of the true pattern of bagginess in the web. A skilled operator can easily determine the correct predetermined tension empirically, but it is very important that the test tension be standardized, since different test tensions will produce different values of dL/L.

Figure 11A:
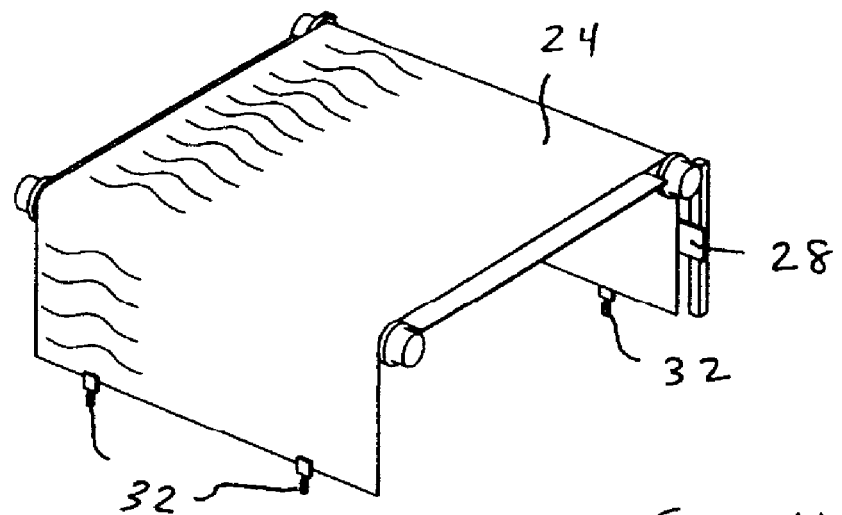
FIGS. 11A and 11B are perspective views showing a web, baggy on one side only, before tension is applied.
Figure 11B:
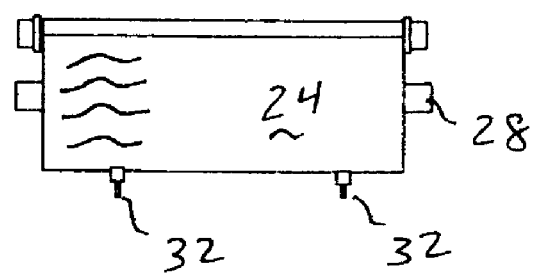
Figure 12A:
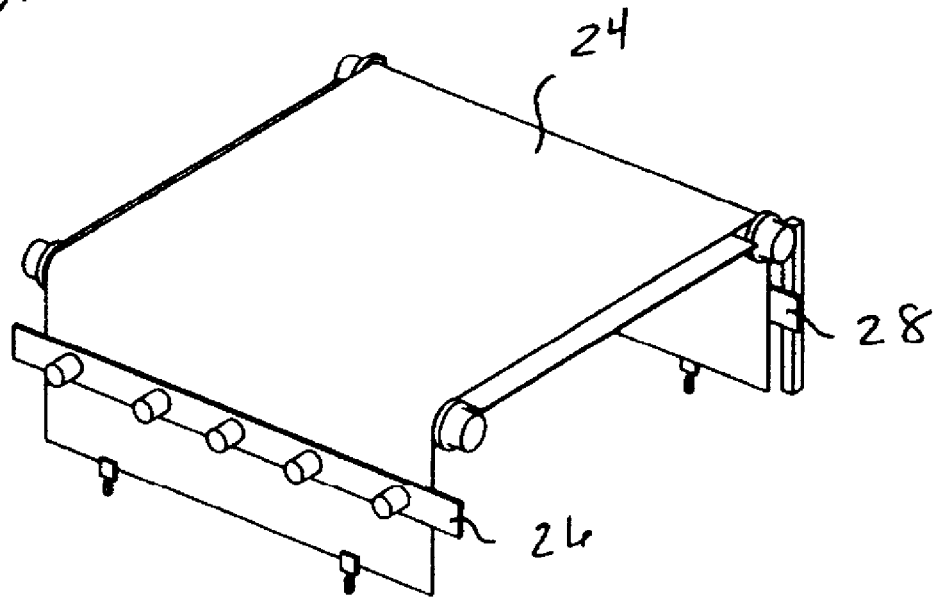
FIGS. 12A and 12B are perspective views showing the same web as in FIGS. 11A and 11B after tension has been incorrectly applied.
Figure 12B:
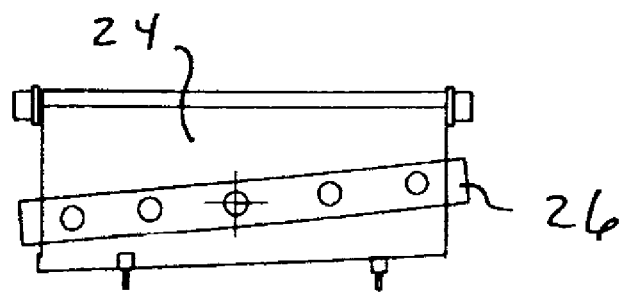
Figure 13A:
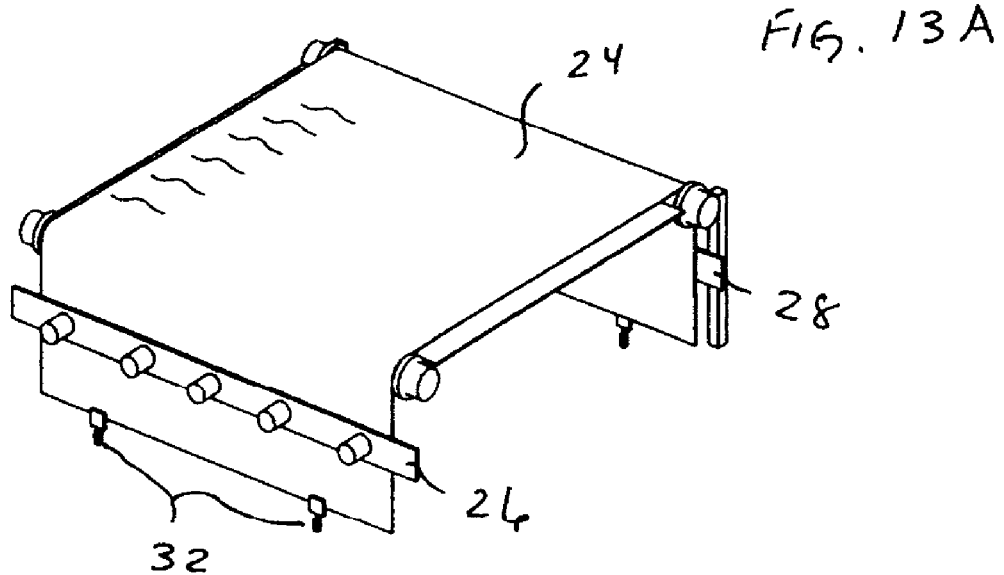
FIGS. 13A and 13B are perspective views showing the same web as in FIGS. 11A and 11B after tension has been correctly applied.
Figure 13B:
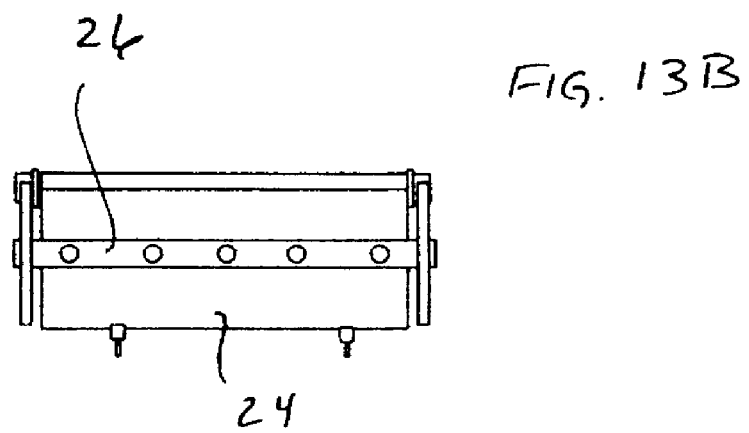

Movable clamp 28 must be drawn downward in pure translation, that is, allowing for no rotation away from its original degree of levelness, during this tensioning step. FIGS. 11A, 11B, 12A, 12B, 13A and 13B illustrate this requirement. FIGS. 11A and 11B show the web before tension is applied. In this example, web 24 exhibits bagginess on one side, represented by the wavy lines on the left side of the web as viewed in the figure. In FIGS. 12A and 12B, movable claim 28 has be applied and drawn downward to tension the web, but the clamp has been allowed to rotate about point "A" of FIG. 12B. Much of the bagginess of the non-tensioned web has been removed and the non-planarity has been masked. In FIGS. 13A and 13B, movable claim 28 has be applied and drawn downward to tension the web. In this case, the clamp has not been allowed to rotate about point "A". The original bagginess of the non-tensioned web has been retained and the non-planarity will show up in the subsequent measurement results.

Figure 14:
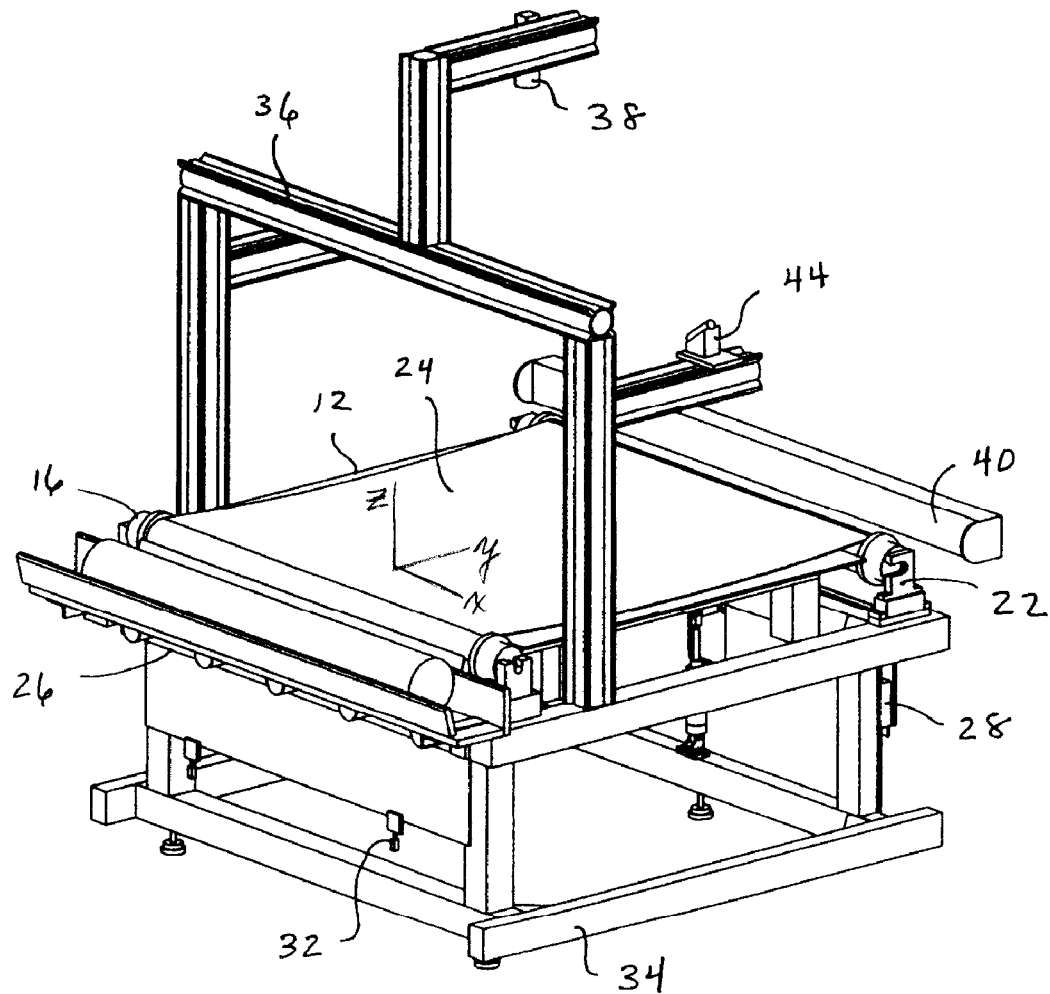
FIG. 14 is a perspective view of the planarity gauge of FIG. 1 further showing upper and lower frame, light sources, and a digital array camera.

Referring now to FIG. 14, the apparatus in accordance with a preferred embodiment of the present invention further includes a lower main frame 34 upon which sits bearing blocks 20 and 21 and load cells 20 of FIG. 1. The lower main frame also supports an upper main frame 36 that carries a digital camera 38 and a pair of opposed laser light sources of which one is visible in the figure. A third, florescent white light source 40 is positioned at the far end of the table 12 in order to create shadowing of any non-planarity when a white-light image is captured by the camera. This serves to document the visual appearance of the tensioned web during the test.

Figure 15:
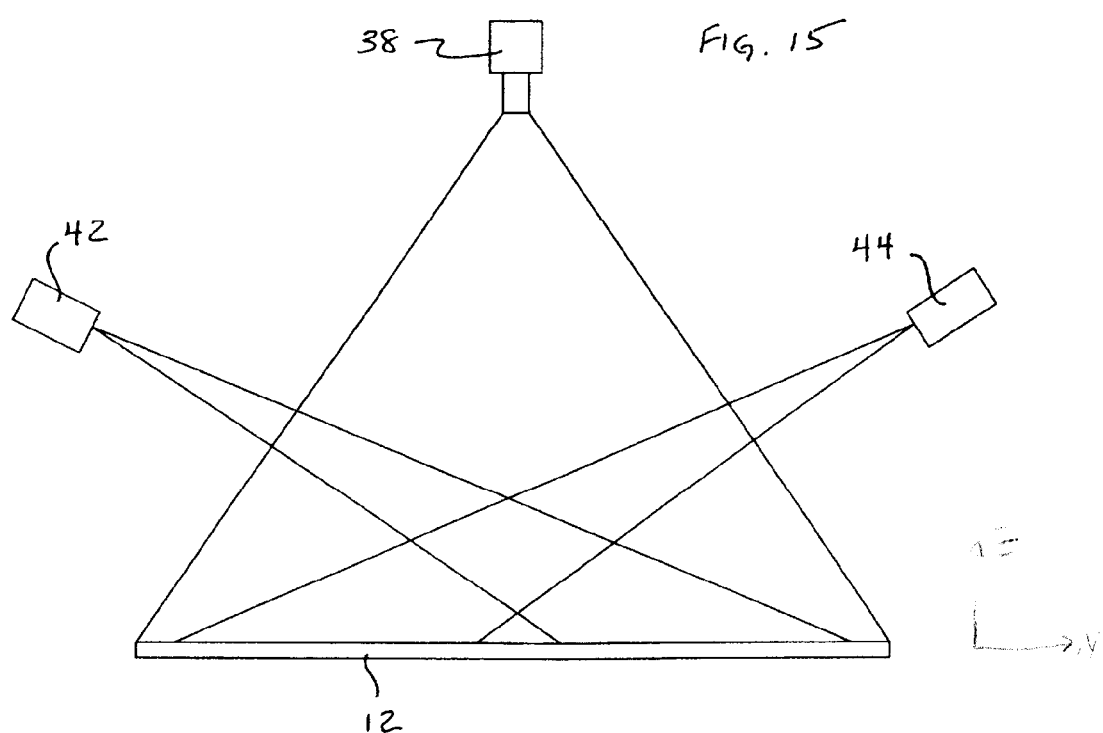
FIG. 15 is a front elevational view showing the position of the light sources and digital camera of FIG. 14, along with the area viewed by the camera, and the areas illuminated by the light sources.

The two laser light sources mentioned immediately above are shown in FIG. 15 and identified by reference numerals 42 and 44. Laser light source 42 on the left side of upper main frame 36 projects a pattern 48 onto the right side of table 12 (see FIG. 16). Laser light source 44 on the right side of upper main frame 36 projects a pattern 46 onto the left side of table 12.

Figure 17:
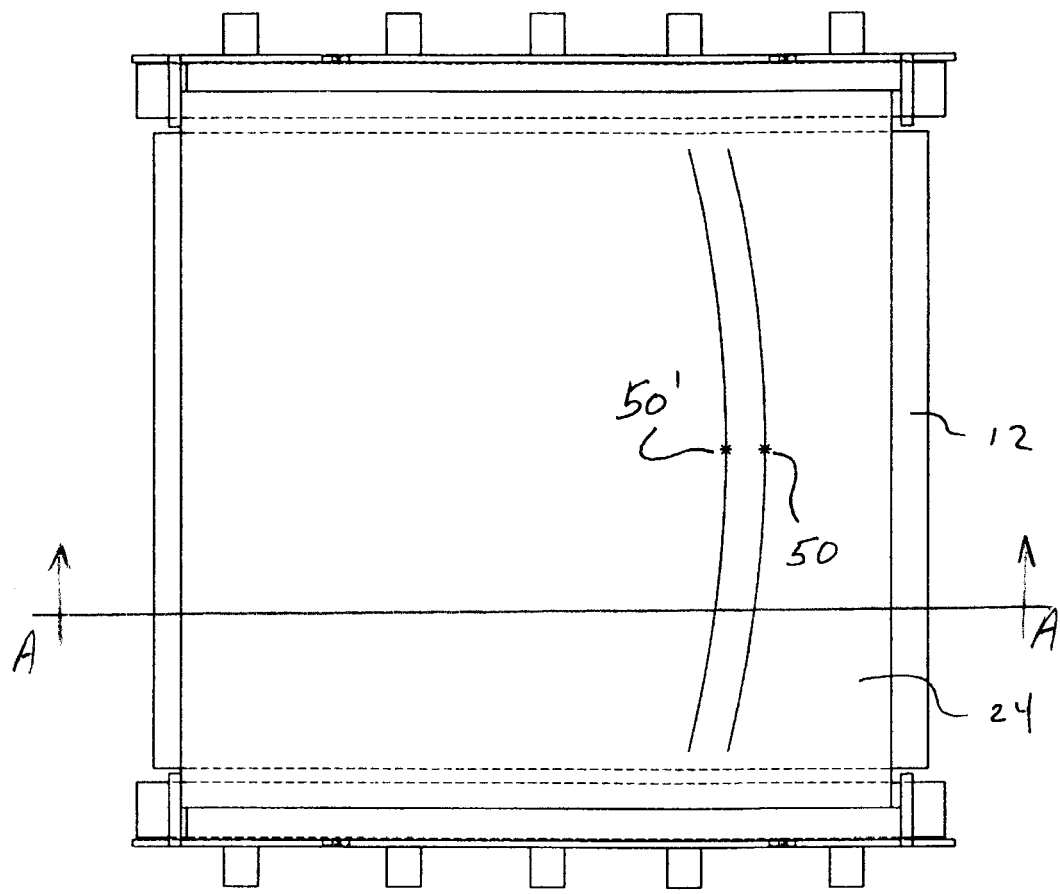
FIG. 17 is a top plan view showing how one such line from one of the light sources shifts laterally when projected onto a perfectly flat but tensioned web.
Figure 18:
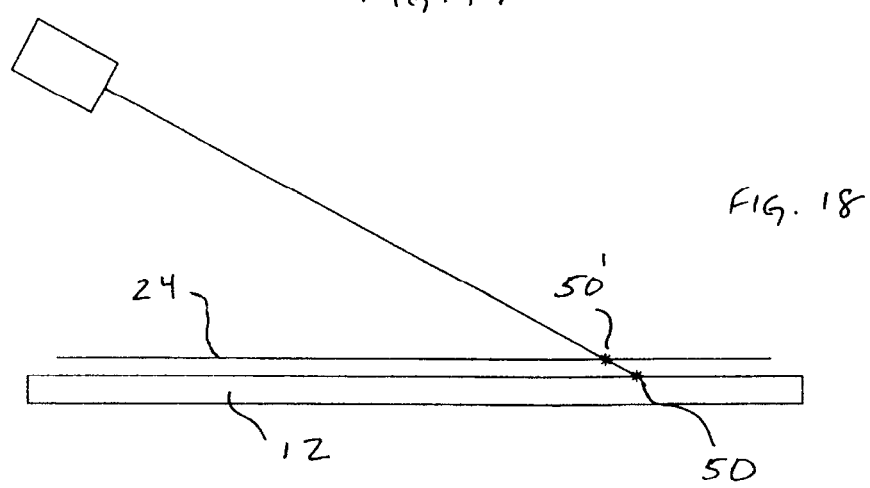
FIG. 18 is a side sectional view taken along line A-A of FIG. 17.

FIGS. 17 and 18 illustrate the result, for a single line in the pattern, of changing between illuminating table 12 with laser light source 42 and illuminating web sample web 24 with that light source. FIG. 17 is the image viewed by digital camera 38. When web 24 is not present, light source 42 projects a pattern 48 of lines, of which one 50 is illustrated. When web 24 is present, the light source projection moves to position 50'. The horizontal positional distance between projection line 50 and projection line 50' as viewed by digital camera 38 is a function of the vertical height of sample web 24 above the reference plane of table 12.

Figure 16:
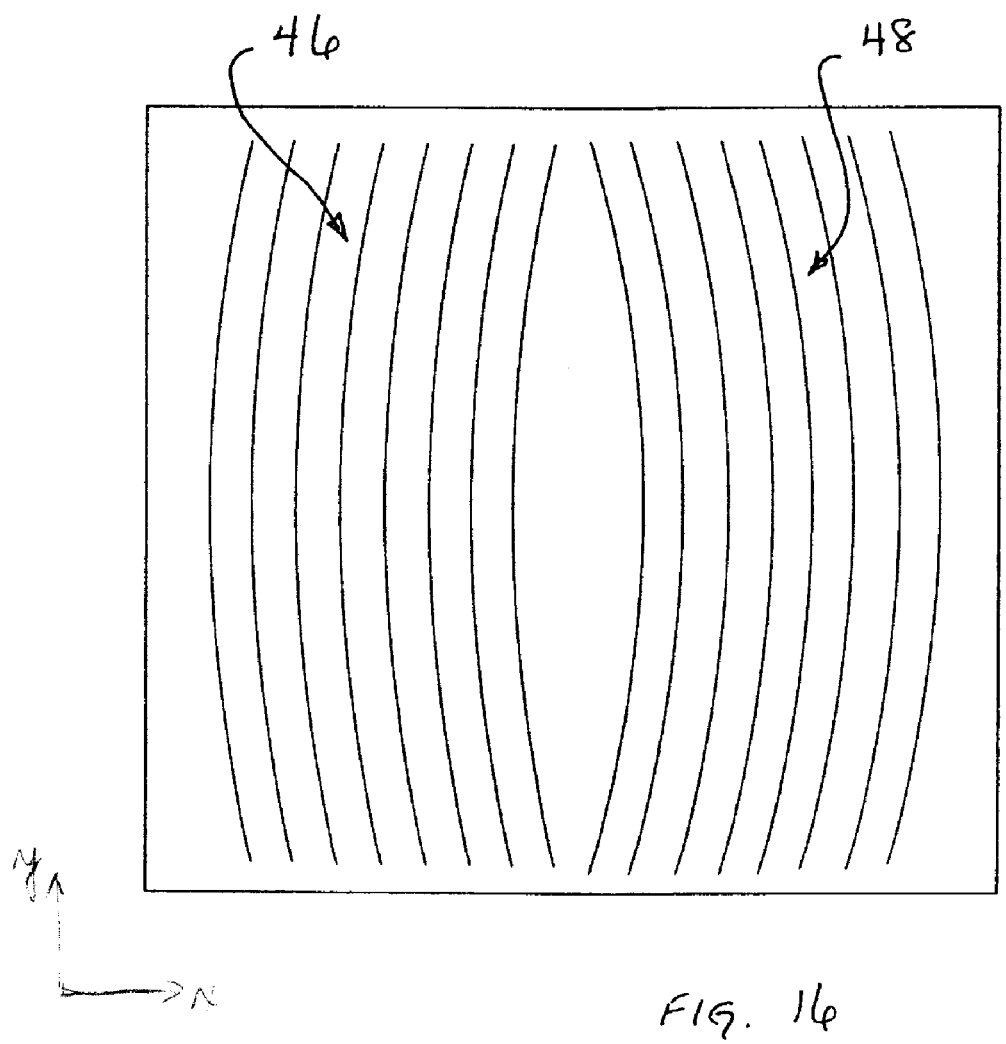
FIG. 16 is a top plan view showing the light patterns from the light sources of FIGS. 14 and 15.
Figure 19:
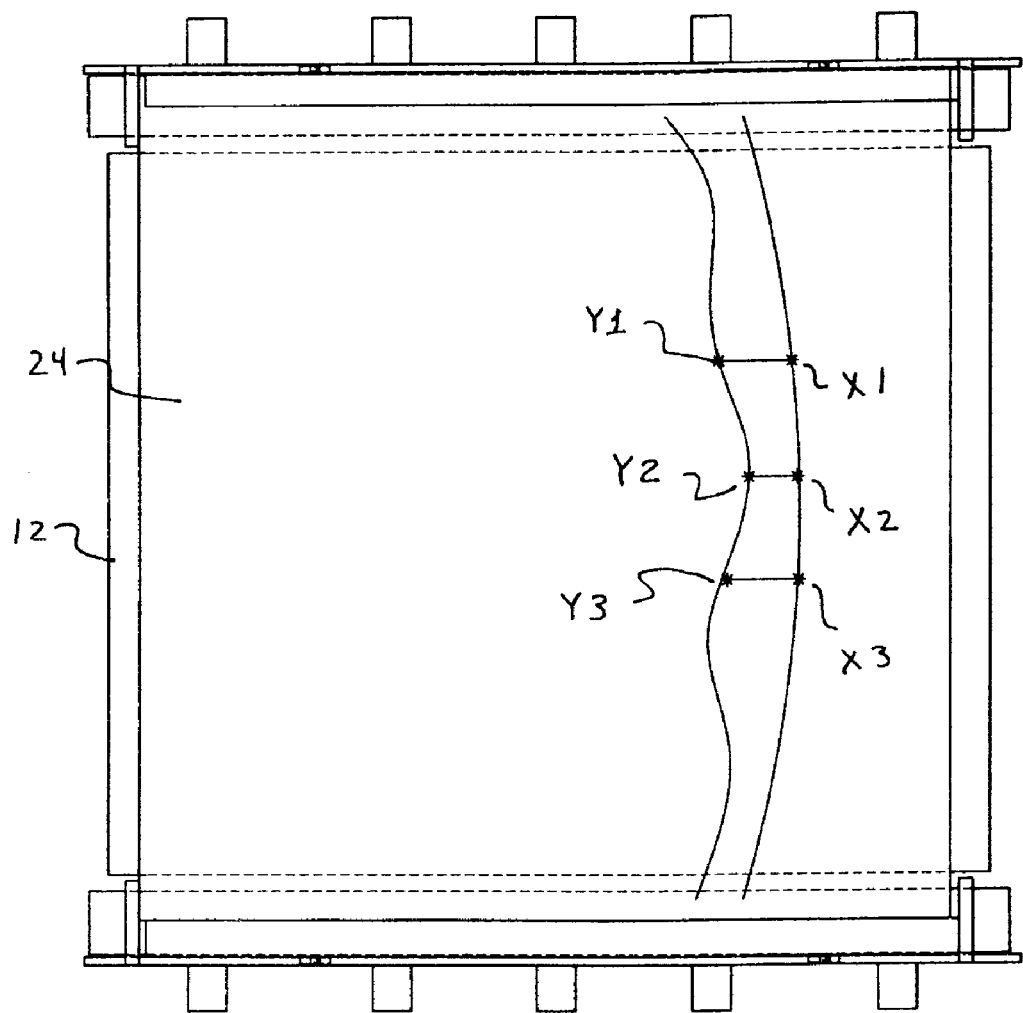
FIG. 19 is a view similar to FIG. 17 showing how one such line from one of the light sources shifts laterally when projected onto a baggy tensioned web.

The patterns shown in FIGS. 16 and 17 represent the projection pattern from the light sources directly onto the table with no web. If sample web 24 was perfectly planar, the patterns would look similar but both would be shifted equally toward the center of the table. FIG. 19 is an illustration of what a projection line 50' might actually resemble if the sample web was non-planar. Projection line 50' appears wavy from above because the horizontal position of the line shifts as a function of the height of the sample web above table 12. Positions X1, X2 and X3 are observed (by camera 38) of line 50 on table 12. Positions Y1, Y2 and Y3 are observed positions on non-planar web 24. Accordingly, the differences between the lengths Y1-X1, Y2-X2, and Y3-X3 are indications of the amount of non-planarity of web 24 at specific positions of the web.

Figure 20:
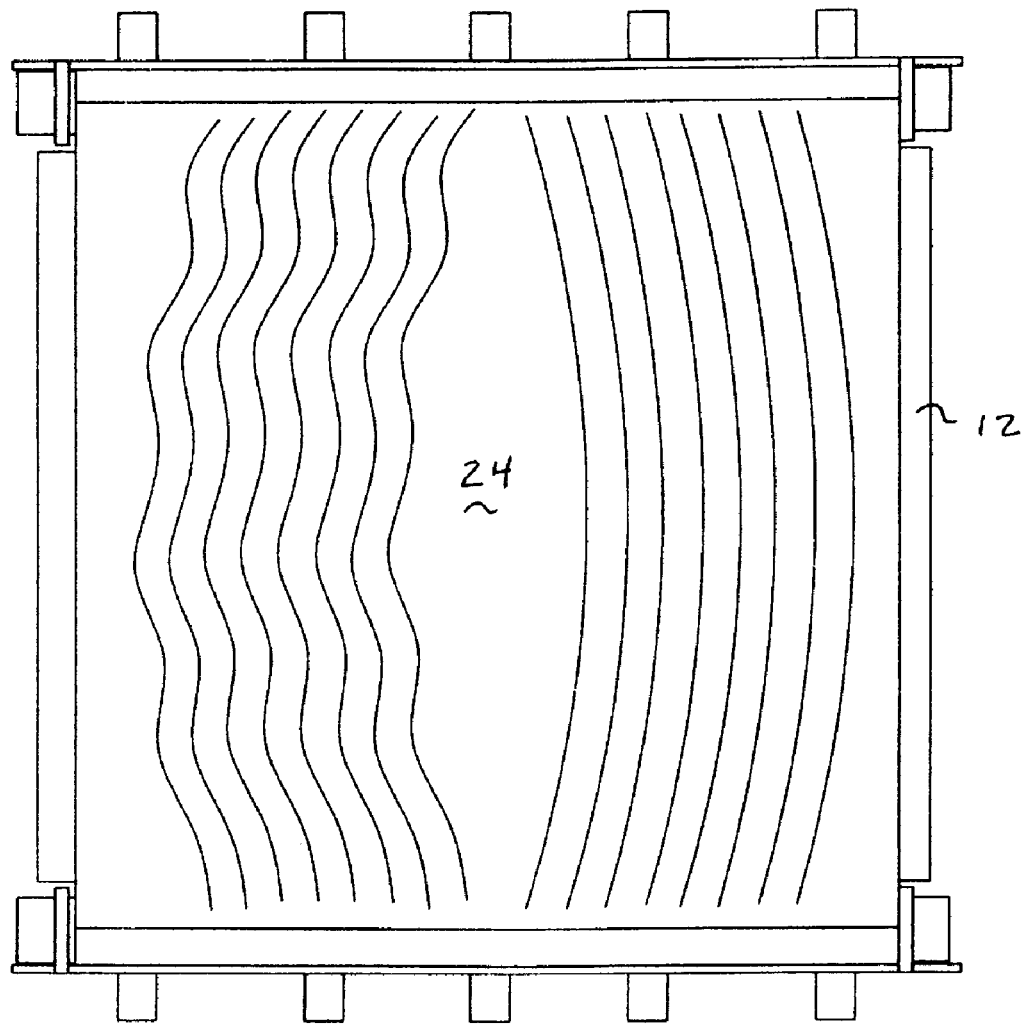
FIG. 20 is an illustration of how the projected light patterns might appear in the sample illustrated in FIG. 11A, where the web illustrates bagginess on the left side but not on the right.
Figure 21:
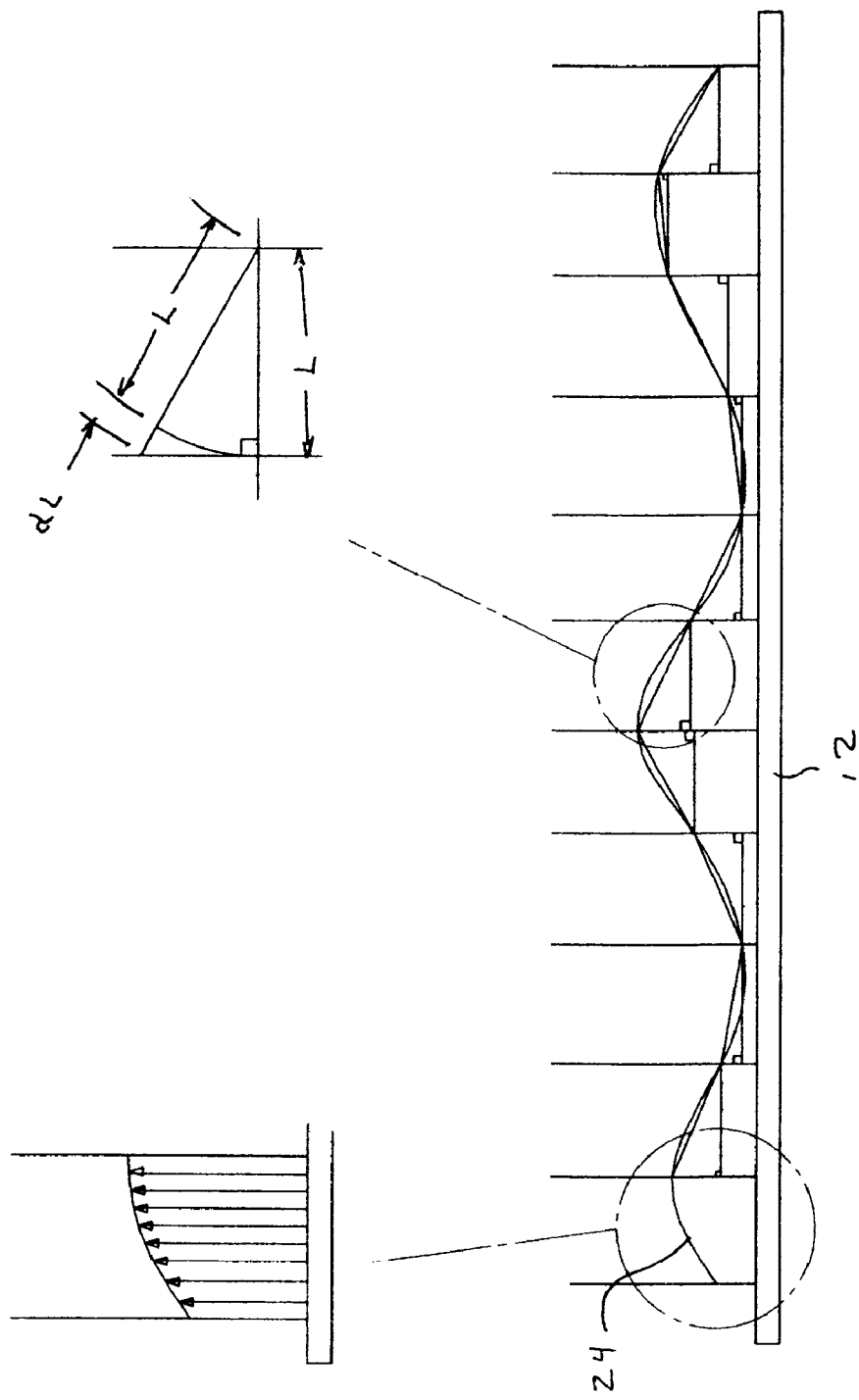
FIG. 21 is a side sectional view taken through the baggy web on the left side of FIG. 20 showing the fundamental parameters used to define bagginess, or non-planarity.
Figure 22:
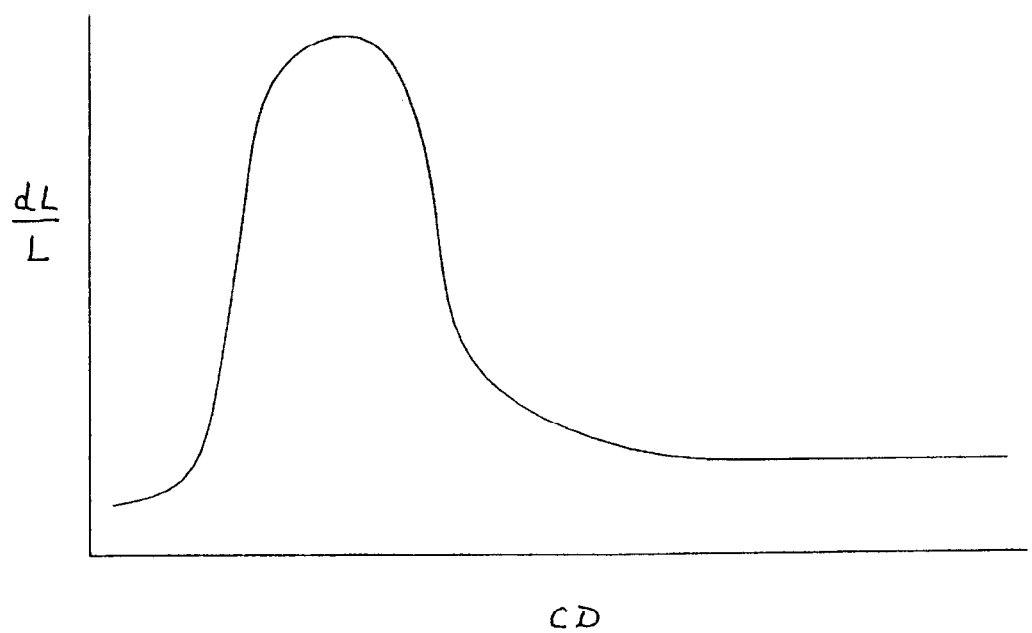
FIG. 22 is a graph of a cross-web planarity profile of a web having one area of non-planarity or one baggy lane.
Figure 23:
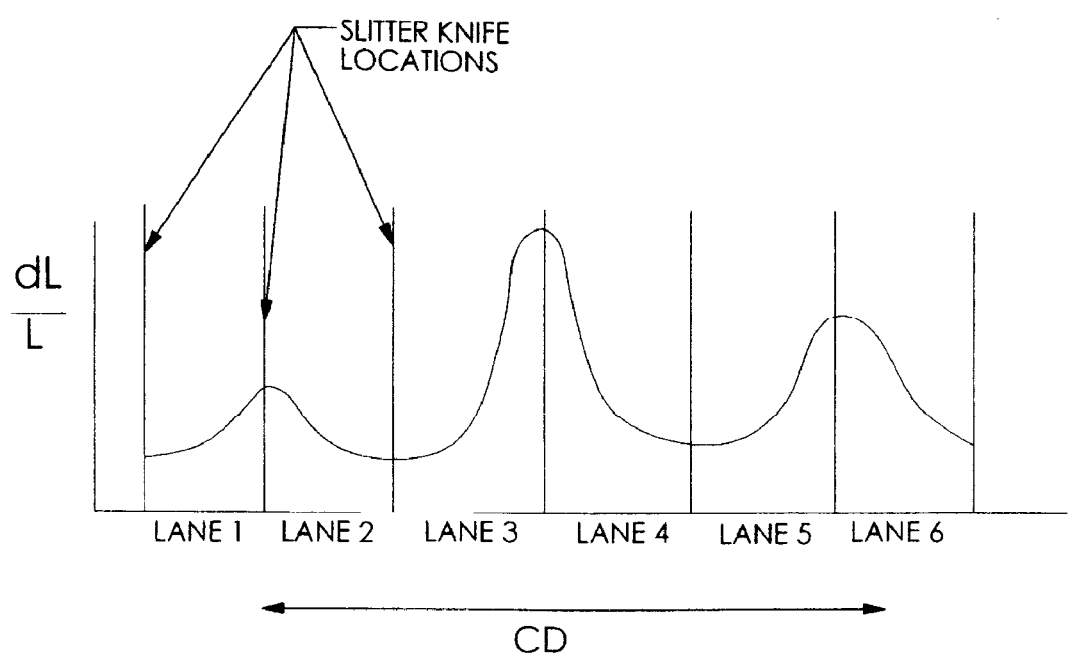
FIG. 23 is a graph of a cross-web planarity profile of a web having three areas of non-planarity or three baggy lanes, and how the non-planarity is distributed across multiple slit lanes during converting.

FIG. 20 is an illustration of how the projected light patterns might appear in the sample illustrated in FIG. 11A, where the web illustrates bagginess on the left side but not on the right. Referring to FIG. 21, the pattern of projected lines allows for an analytical measurement of bagginess. First, for each right triangle, the differential length between the hypotenuse and the adjacent side is defined as dL. Pluralities of samples of these differential lengths are taken along a sample length at finite cross-web directional positions. A fundamental measure of non-planarity dL/L for each cross-web directional position is obtained by summing all of these differential lengths dL over the machine direction sample length (say, 36" in a preferred embodiment), and then dividing by the sample length. Finally, a cross-web planarity profile is developed by plotting the measure of non-planarity dL/L for each cross-web directional location as a function of the cross-web directional location. The result of the sample of FIG. 20 might look like the plot shown in FIG. 22, where there is only one large area of non-planarity or one wide baggy lane. The result of a different sample might look like the plot shown in FIG. 23, where there are three areas of non-planarity or three baggy lanes.

Figure 24:
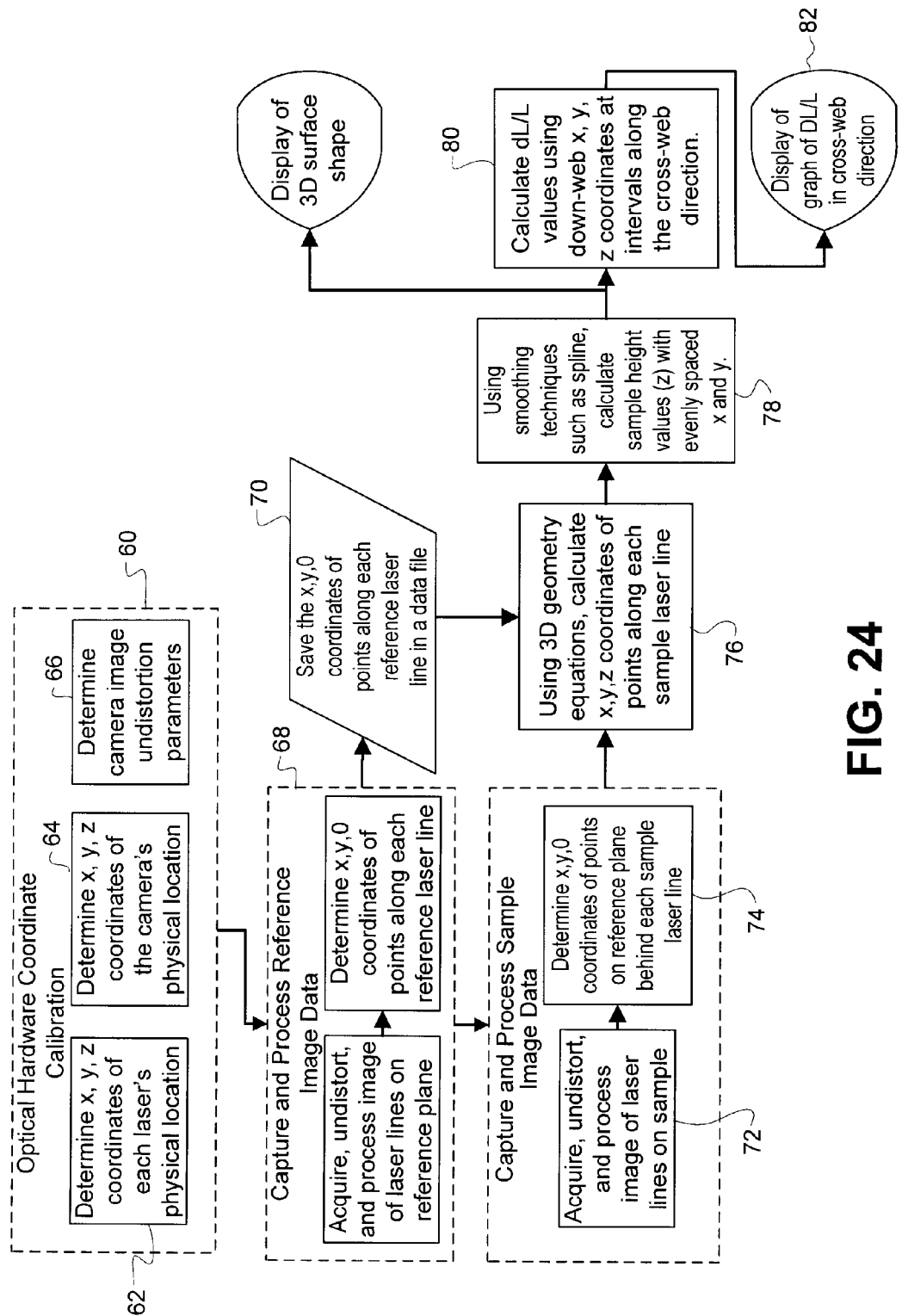
FIG. 24 sets forth the recommended steps to be taken practicing the preferred embodiment of the present invention

FIG. 24 sets forth the recommended steps to be taken practicing the preferred embodiment of the present invention. From time to time, the optical hardware should be calibrated, as represented in box 60. One should determine the location of each laser light source 42, 44 and digital camera 38 relative to the rest of the structures; STEP 62. The location of the light source and camera origins relative to the top of table 12 are important for the proper calculation of web height above the table; STEP 64. Numerical constants describing these locations are easily determined by placing calibration fixture(s) of known height on top of the reference tabletop. A sufficient number of calibration positions are needed to reduce the light source and camera position errors to an acceptable level. A "Least-Squares" calibration method works well. Like the tabletop, the fixture plates are preferably painted white for maximum reflectivity. The image distortion, commonly called 'barrel' distortion, that would be introduced by the lens of camera 38 should be determined so that parameters can be developed to compensate for the distortion; STEP 66.

Once calibration is complete, a reference image is captured (STEP 68) to determine the coordinates of various points along the laser lines on the top of table 12 without a sample web 24 present. The determined coordinates of each point are saved; STEP 70.

Once a sample is properly aligned as described above, the laser lines are again sampled (STEP 72) and the coordinates of the points on the reference plane are determined for each sample laser line; STEP 74. Comparing the sample data and the reference data, and using conventional three dimensional geometry equations, the spatial coordinates of the points along each sample laser line are calculated; STEP 76. The results are smoothed and height above the table values are recalculated at evenly spaced points along x and y (STEP 78). Finally dL/L values are calculated along the MD sample length using x, y and z coordinates at finite intervals along the cross-web direction (STEP 80), and are displayed in graphical form at STEP 82

The invention has been described in detail with particular reference to certain preferred embodiments thereof, but it will be understood that variations and modifications can be effected within the spirit and scope of the invention.

PARTS LIST

10 near roller
12 table
14 far roller
16 guide flange
17 guide flange
18 guide flange
19 guide flange
20 bearing block
21 bearing block
22 load cells
24 web sample
26 stationary clamp
28 movable clamp
30 clamping air cylinders
32 preload weights
34 lower main frame
36 upper main frame
38 digital camera
40 florescent white light source
42 laser light source
44 laser light source
46 pattern
48 pattern
50 projection line on table
50' projection line on web
60 calibration box
62 light source location determination step
64 camera location determination step
66 image distortion parameter determination step
68 reference image capture and processing step
70 reference line coordinates save step
72 sample image capture and processing step
74 coordinate determination step
76 coordinate calculation step
78 heights calculation step
80 calculation of dL/L step
82 display dL/L profile step

What is claimed is:

1. An apparatus for measuring web planarity, comprising:
a reflective reference surface lying in a horizontal plane;
a light source adapted to project a light pattern onto the reference surface along a non-vertical axis, said light pattern having discrete regions that intercept the reference surface;
a support adapted to receive a web and to bear the received web vertically offset from the reference surface such that the received web intercepts the discrete regions of the projected light pattern; and
an imaging device adapted to:
  detect (1) positions on the reference surface of interception of the discrete regions of the projected light pattern and (2) respective positions on the received web of interception of the same discrete regions of the projected light pattern,
  determine the vertical offset of the respective positions on the received web as a function of differences in the detected positions on the reference surface and the respective detected positions on the received web, and
  calculate a measure of non-planarity of the received web based upon a comparison of a plurality of such vertical offsets from a plurality of detected positions of the received web.

2. An apparatus for measuring web planarity as set forth in claim 1 wherein the support is a pair of parallel rollers on opposed sides of the reference surface.

3. An apparatus for measuring web planarity as set forth in claim 1 wherein the support further comprises a tensioner for applying a predetermined tension to the web.

4. An apparatus for measuring web planarity as set forth in claim 3 wherein the tensioner comprises a pair of clamps, at least one of which is movable.

5. An apparatus for measuring web planarity as set forth in claim 1 wherein the imaging device comprises a digital camera.

6. An apparatus for measuring web planarity as set forth in claim 5 wherein the digital camera is carried on a frame above the reference surface.

7. An apparatus for measuring web planarity as set forth in claim 1 wherein the light source is adapted to project a plurality of lines on the reference surface, said lines comprising the projected light pattern.

8. An apparatus as set forth in claim 7 wherein the light source comprises two light sources with criss-crossing light patterns so as to increase spatial resolution of the measurements in the cross-web direction.

9. An apparatus for measuring web planarity as set forth in claim 1 wherein the light source is a laser.

10. A method of measuring web planarity, comprising the steps of:
providing a reflective reference surface and adjusting the reference surface to be level in a horizontal plane;
projecting a light pattern of discrete regions onto the reference surface along a non-vertical axis so as to intercept the reference surface;
supporting a web spaced vertically above the reference surface such that the received web intercepts the discrete regions of the projected light pattern;
detecting positions on the reference surface of interception of the discrete regions of the projected light pattern;
detecting respective positions on the received web of interception of the same discrete regions of the projected light pattern;

determining the vertical offset of the respective positions on the received web as a function of differences in the detected positions on the reference surface and the respective detected positions on the received web; and calculating a measure of non-planarity of the received web based upon a comparison of a plurality of such vertical offsets from a plurality of detected positions of the received web.

11. A method of measuring web planarity as set forth in claim 9 wherein the support step includes tensioning the web.

* * * * *